United States Patent

Gabelli

[11] Patent Number: 4,677,854
[45] Date of Patent: Jul. 7, 1987

[54] TEST DEVICE FOR PRODUCING A BIAXIAL STATE OF TENSION

[75] Inventor: Antonio Gabelli, Ijsselstein, Netherlands

[73] Assignee: SKF Industrial Trading and Development Company B.V., Netherlands

[21] Appl. No.: 816,429

[22] Filed: Jan. 6, 1986

[30] Foreign Application Priority Data

Jan. 22, 1985 [NL] Netherlands ............... 8500151

[51] Int. Cl.⁴ ................................ G01N 3/00
[52] U.S. Cl. ................................ 73/794; 73/831
[58] Field of Search ............ 73/794, 838, 795, 826, 73/831, 834, 835, 837; 69/19.3, 19.2, 19.1

[56] References Cited

U.S. PATENT DOCUMENTS

| 1,851,020 | 3/1932 | Schettler | 69/19.3 |
| 3,807,224 | 4/1974 | Hassenboehler | 73/831 |
| 4,438,570 | 3/1984 | Dokupil | 69/19.3 X |

Primary Examiner—Jerry W. Myracle
Attorney, Agent, or Firm—Eugene E. Renz, Jr.

[57] ABSTRACT

Apparatus for producing a biaxial state of tension in a flat body in the form of a thin test specimen made of an elastic material comprising a plurality of clamping members adapted to be detachably secured to the periphery of the test body, a drawplate (15), elements connecting the clamping members to the drawplate including force transmitters in the form of cables, each cable connected at one end to a clamping member and at its opposite end by adjustable and removable elements to the drawplate, rerouting wheels (10) directing the cables (9) from the drawplate to the clamps to thereby distribute a uniaxial force on the drawplate uniformly to the clamping members via the rerouting wheels.

4 Claims, 3 Drawing Figures

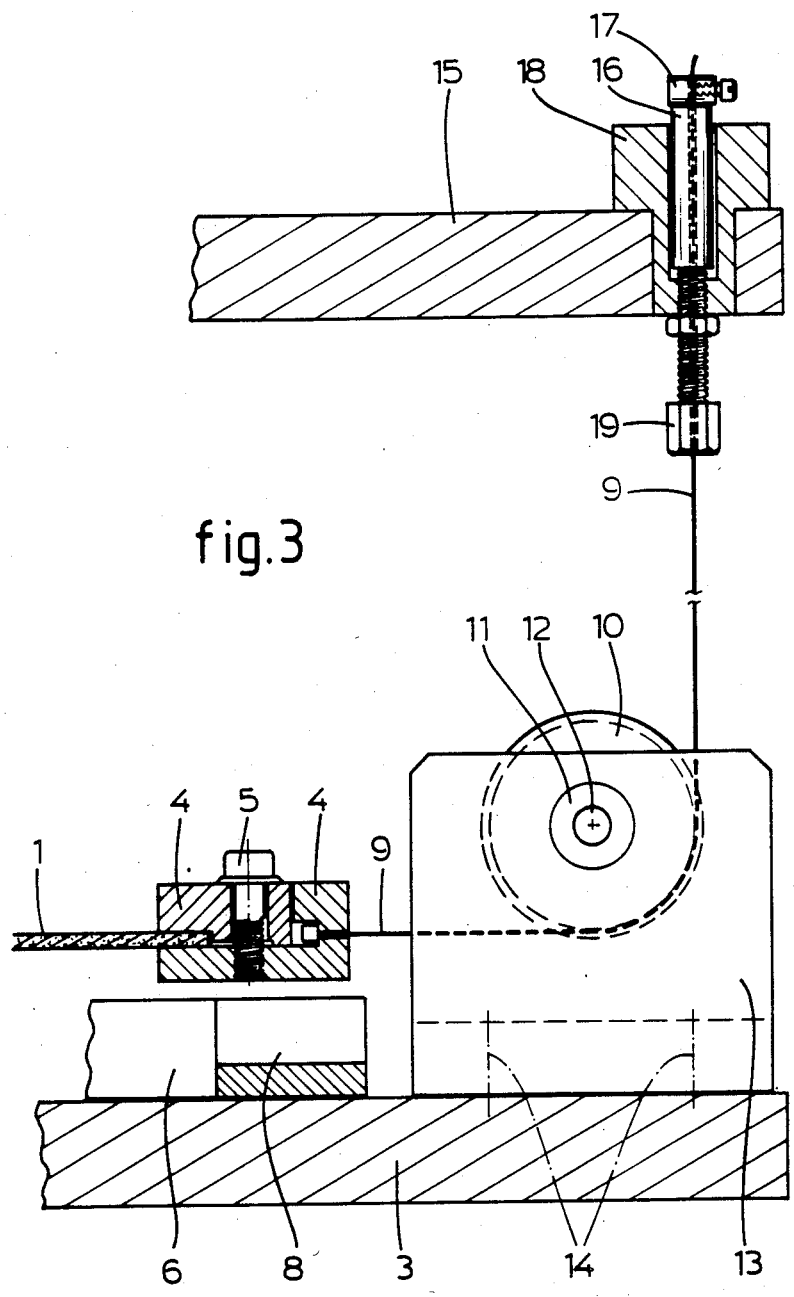

TEST DEVICE FOR PRODUCING A BIAXIAL STATE OF TENSION

FIELD OF THE INVENTION

The invention relates to a device for producing a biaxial state of tension in a flat body, in particular in a thin rubber test specimen, provided with a plurality of clamps capable of attachment to the periphery of the body, each of which transmits to the body a force acting in a given direction in the plane of the flat body.

BACKGROUND OF THE INVENTION

Such a device is already known and is used, among other things, for testing the elongation properties of rubber under this state of tension.

This known device is provided with two pulling elements arranged perpendicular to one another. A rubber test specimen is capable of being placed in the plane of the stress to be produced. Two adjacent sides of the plate are connected with the pulling elements, the tensile force thereof being perpendicular to the associated side. The two other sides are fixed, in the direction of the force exerted on the opposing side, by a stationary part of the device.

This known device is very complex and therefore costly. In addition, the two pulling elements must exhibit a very good synchronous action together in order to obtain accurate and reproducible test results.

The object of the invention is to procure a device of the sort mentioned at the beginning wherein the drawbacks described above are effectively eliminated.

To this end, the device according to the invention is characterized in that one drawplate is provided, while force transmitters distribute a uniaxial force exerted on the drawplate via rerouting elements over the clamps.

The means accordingly need not have any specially designed pulling elements, but may be placed in a standard draw bench, which makes the entire test setup simpler and cheaper.

In addition, there are no longer any problems of synchronization, because only a single force is exerted.

Further, it is no longer necessary to use a square test specimen, as the direction of the tensile force at the clamps, owing to the rerouting elements, is independent of the direction of the tensile force at the drawplate.

In a favorable embodiment of the device according to the invention the clamps are mounted with a regular distribution, being radially displaceable, and the clamps are preferably placed in a circular arrangement. In this way a circular rubber disk may be utilized as test specimen. This has the advantage that a purely radial state of tension is produced, where the force transmitted by the clamps to the body lies in line with the displacement of the clamp caused by the deformation of the body.

The lateral displacement of the clamp necessary when a square test specimen is stressed, which is produced owing to the fact that the direction of the deformation and the force do not coincide, does not occur in this embodiment.

Owing to this the special provisions which make such lateral displacement possible are omitted, so that the device may be even more simply designed.

An advantageously applicable embodiment of the device according to the invention is characterized in that the uniaxial force exerted on the drawplate is at least approximately perpendicular to the plane of the body to be stressed.

In this way a rotationally symmetric arrangement may be obtained, which has a positive influence on the accuracy of the state of tension produced.

In an advantageously applied embodiment of the device according to the invention the force transmitters consist of cables, while the rerouting elements are designed as rerouting wheels which reroute the cables from the drawplate to the clamps.

BRIEF DESCRIPTION OF THE DRAWINGS

The invention is explained below with the aid of a drawing representing an example of the device according to the invention.

FIG. 3 is a portion of the side view of FIG. 2, on a larger scale.

DESCRIPTION OF THE PREFERRED EMBODIMENT

Figure 1:
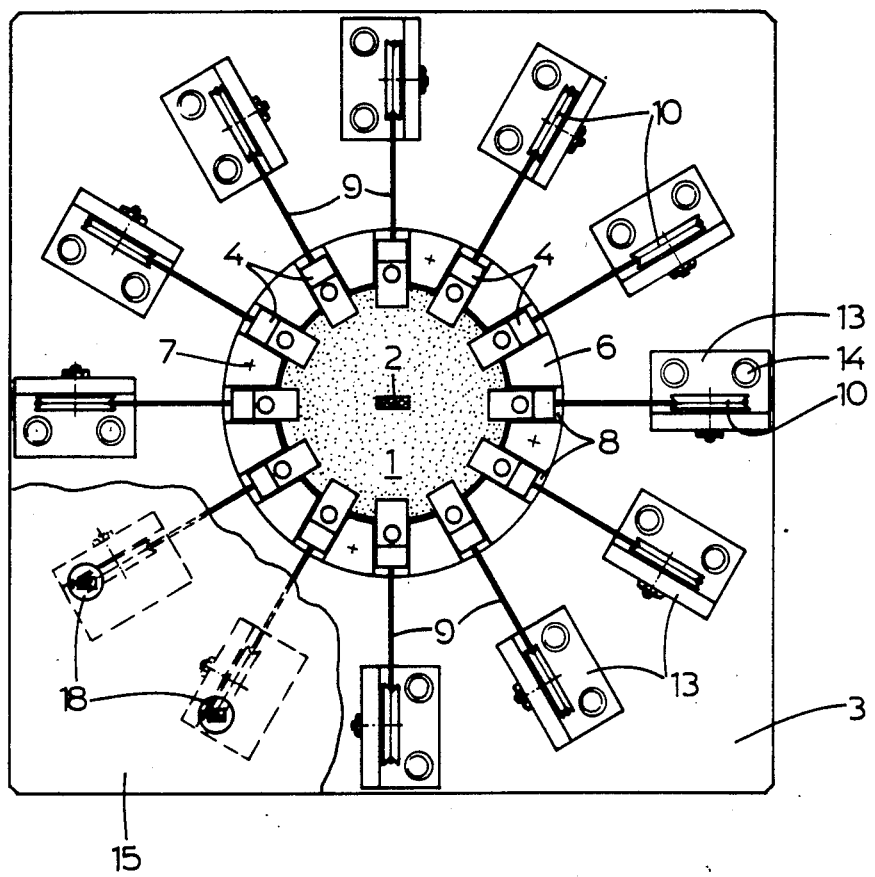
FIG. 1 is a top view of a device according to the invention wherein part of the top side is cut away.
Figure 2:
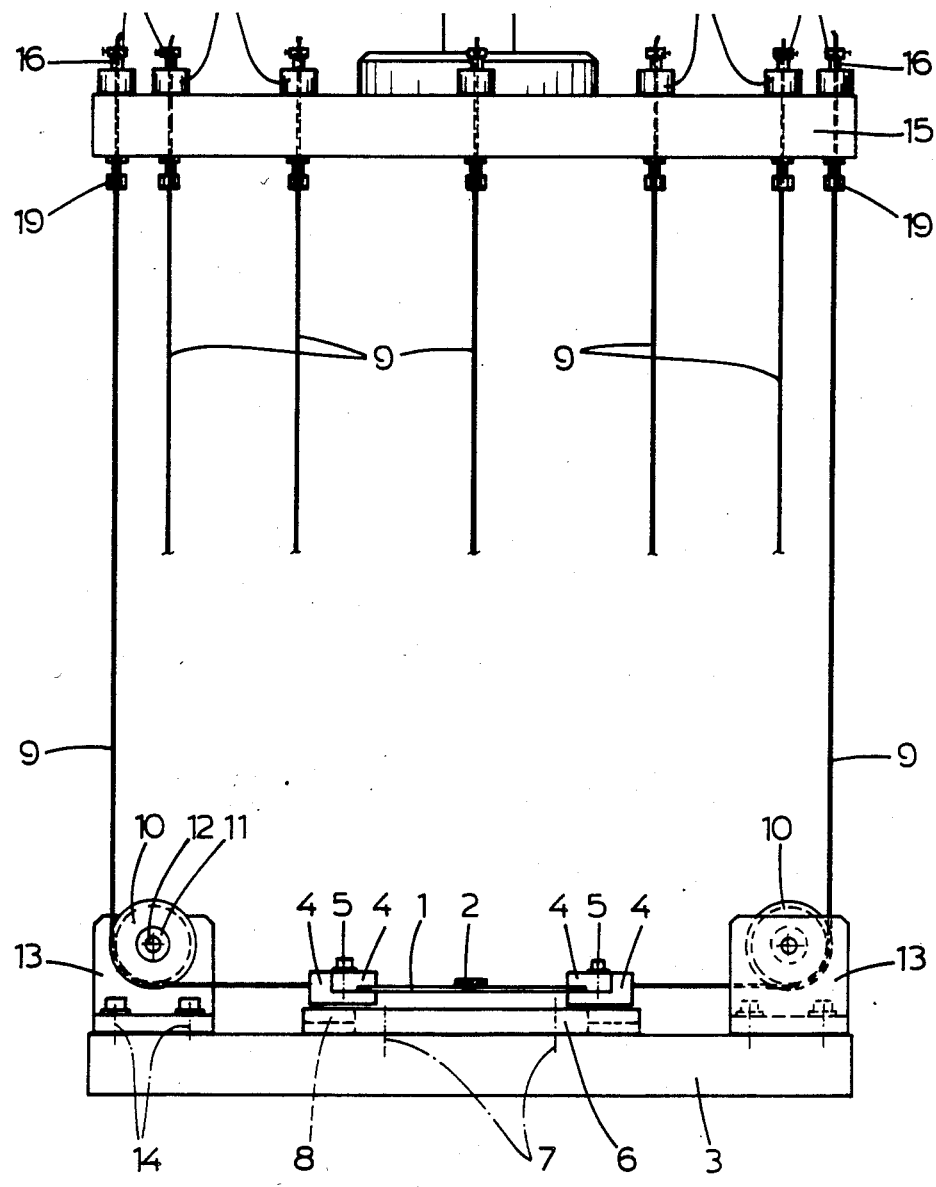
FIG. 2 is a schematic side view of the device of FIG. 1.

In the drawing is represented an embodiment of the invention wherein a test specimen 1, designed as a circular disk, is clamped into the device. On this test specimen 1 are provided elongation strips 2, by which the extension of the test specimen may be measured.

The test specimen 1 is arranged parallel to a table 3 running horizontally. On the periphery of the test specimen 1 are mounted, with a proportional distribution, clamps 4, which are clamped to the test specimen by bolts 5.

In order to be able to place all clamps accurately on the periphery of the circular test specimen 1, an auxiliary piece 6 is fastened to the table 3 with bolts 7. This auxiliary piece 6 is provided with recesses 8 into which the clamps fit accurately. In stressed state of the test specimen 1, however, the clamps 4 run above the auxiliary piece 6 and no longer make contact with it.

The ends of cables 9 are secured in the clamps 4. Each cable 9 runs radially from the test specimen 1 to an associated rerouting wheel 10 which deflects the cable 9 in a direction perpendicular to the plane of the test specimen 1.

Each rerouting wheel 10 is seated by a ball bearing 11 on a shaft 12 which runs parallel to the plane of the test specimen 1 and which likewise runs parallel to the tangent to the test specimen 1 at the associated clamp 4.

Each shaft 12 is mounted in a support 13, which is fastened to the table 3 with bolts 14. Lastly, the table 3 is fitted on the fixed part of a draw bench, not represented.

After the rerouting wheels 10 the cables 9 run parallel to one another to a horizontally suspended drawplate 15, which is coupled by a universal joint with the part of the draw bench displaceable perpendicular to the plane of the test specimen 1.

Each cable 9, at the drawplate 15, is conducted through a bushing 16 and above the bushing 16 is blocked against retraction by a cable clamp 17. The bushing 16 is placed slidable in a bushing 18, which in turn is fitted in the drawplate 15. A hollow set screw 19, running about the cable 9, is screwed into the bushing 17 from underneath and is able to push the bushing 16 upward, in order to tension the cable 9 conducted through it. In this way all cables 9 may be brought to like tension, so that when the test specimen 1 is stressed, each clamp 4 exerts an equally great force on the test specimen 1.

The invention is not limited to the example represented in the drawing, which may be varied in different ways within the scope of the invention.

What is claimed is:

1. Apparatus for producing a biaxial state of tension in a flat body (1) in the form of a thin test specimen made of an elastic material comprising a plurality of clamping members (4) adapted to be detachably secured to the periphery of the test body, a drawplate (15), means connecting the clamping members to the drawplate including force transmitters in the form of cables, each cable connected at one end to a clamping member (4) and at its opposite end by adjustable and removable means to the drawplate, rerouting wheels (10) directing the cables (9) from the drawplate to the clamps to thereby distribute a uniaxial force on the drawplate uniformly to the clamping members via the rerouting wheels and a plurality of aligning members (6) for removably receiving the clamping members to provide means for accurately positioning the clamping members on the periphery of the test body.

2. Apparatus for producing a biaxial state of tension in a flat body (1) in the form of a thin test specimen made of an elastic material comprising a plurality of clamping members (4) adapted to be detachably secured to the periphery of the test body, a drawplate (15), means connecting the clamping members (4) to the drawplate including force transmitters in the form of cables, each cable connected at one end to a clamping member and at its opposite end by adjustable and removable means to the drawplate, rerouting wheels (10) directing the cables (9) from the drawplate to the clamps to thereby distribute a uniaxial force on the drawplate uniformly to the clamping members via the rerouting wheels, said adjustable means comprising a first bushing (16) and cable clamp (17), said first bushing slidable in a second bushing (18) fitted in the drawplate, and screw means surrounding the cable engageable in the first bushing to displace the same and thereby tension the cable.

3. Apparatus as claimed in claim 2, wherein the clamping members (4) are disposed in a circular array.

4. Apparatus as claimed in claim 2, wherein the uniaxial force exerted on the drawplate (15) is at least approximately perpendicular to the plane of the body (1) to be stressed.

* * * * *